Figure 1:
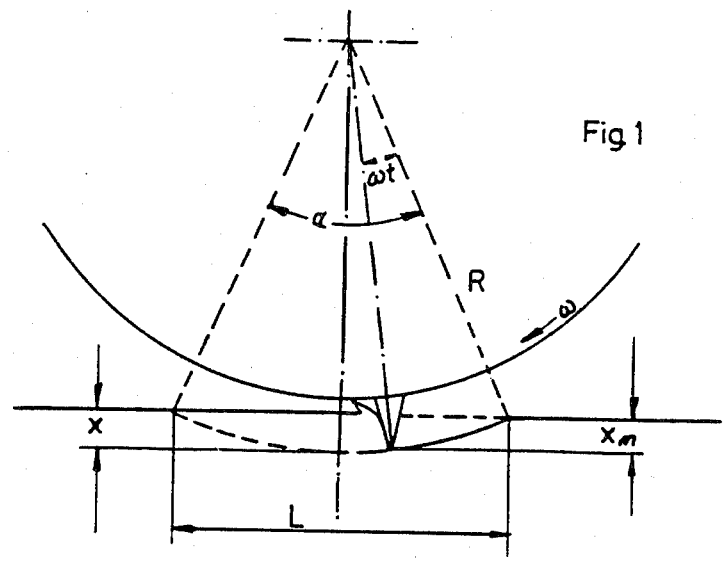

United States Patent [19]

Rehfeld et al.

[11] Patent Number: 4,472,961
[45] Date of Patent: Sep. 25, 1984

[54] APPARATUS FOR TESTING ABRASIVE GRAINS IN SINGLE-GRIT SCRATCH TESTS

[75] Inventors: Gerhard Rehfeld; Klaus Steffens, both of Aachen, Fed. Rep. of Germany

[73] Assignee: Dynamit Nobel AG, Troisdorf, Fed. Rep. of Germany

[21] Appl. No.: 359,970

[22] Filed: Mar. 19, 1982

[30] Foreign Application Priority Data

Mar. 21, 1981 [DE] Fed. Rep. of Germany ....... 3111244

[51] Int. Cl.$^3$ .............................................. G01N 3/56
[52] U.S. Cl. ................................................. 73/7; 73/9
[58] Field of Search ............................ 73/7, 104, 9, 78

[56] References Cited

U.S. PATENT DOCUMENTS 3,214,965 11/1965 Wellborn .................................. 73/7
3,895,526 7/1975 Pozzetti .................................... 73/7

FOREIGN PATENT DOCUMENTS 2054505 2/1978 Fed. Rep. of Germany .......... 73/78

OTHER PUBLICATIONS

Wear (1972), pp. 301–314, Graham and Baul, "An Investigation Into the Mode of Metal Removal in the Grinding Process".

*Primary Examiner*—Charles Frankfort
*Assistant Examiner*—Denis E. Corr
*Attorney, Agent, or Firm*—Felfe & Lynch

[57] ABSTRACT

An apparatus adapted to be mounted on a surface grinding machine is provided for testing abrasive grains in single-grit scratch tests. To permit specimen preparation and scratching to be carried out on a single machine without changeover and without reclamping the specimen, and to maintain the infeed in the scratching operation constant by giving the specimen a contour corresponding to the cross-feed error, a belt grinder and a scratching device comprising a support disk, mounted by means of a main flange and a counterflange, and a scratching disk mounted on the main flange and carrying a single grain secured to its periphery along with a force-measuring system disposed thereunder, are designed as a structural unit adapted to be mounted on the spindle of the surface grinding machine, with a belt tensioning arm mounted to the headstock. The requisite natural frequency of the force-measuring system is obtained by locating a grain holder, a piezoelectric quartz crystal and a necked-down titanium bolt with rapid-acting tightening means on the rotating scratching disk beneath the abrasive grain.

2 Claims, 4 Drawing Figures

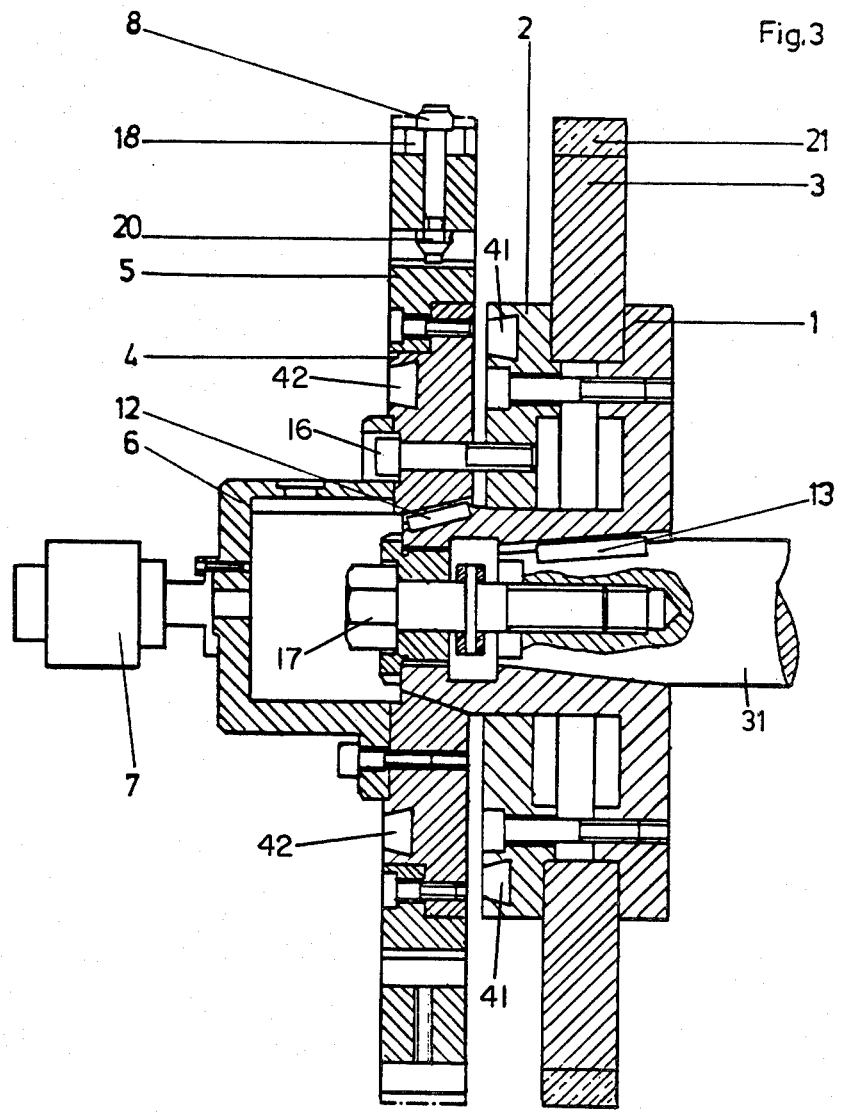

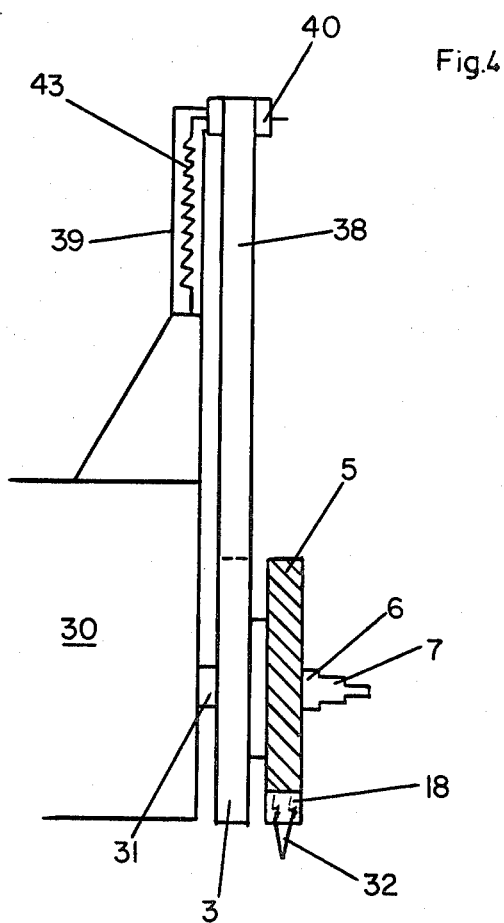

APPARATUS FOR TESTING ABRASIVE GRAINS IN SINGLE-GRIT SCRATCH TESTS

The invention relates to an apparatus for testing abrasive grains in single-grit scratch tests which is suitable for mounting on a surface grinding machine.

The wear and cutting behavior of abrasive grains can be investigated by means of single-grit scratch tests. The scratching process with a grain undergoing testing which is held in a mounting fixture on the periphery of a cylindrical disk that is concentric about its axis is represented diagrammatically in FIGS. 1 and 2 of the drawing.

The single-grit scratch test permits an exact study of the wearing processes and cutting behavior of different types of grains. In order that the test may duplicate the conditions prevailing in actual practice, the kinematics of the grinding operation should be reproduced so far as cutting speed and path are concerned. The meaningfulness of such tests depends not only on the manner in which they are performed and in which the test results are interpreted and evaluated but also, and in large measure, on the testing apparatus used.

The feasibility of such scratch tests depends on the availability of suitable equipment. A primary requirement is a scratching device which satisfies the conditions outlined below.

Single-grit scratch tests are usually run on surface grinders. Now since these machines are generally converted to scratching only temporarily, for economic reasons, and must be available the rest of the time for their actual purpose, which is grinding, such changeover must be readily accomplished. This is the case when the scratching device can be mounted on the spindle of the surface grinder much like a grinding wheel with its flanges.

An important factor in single-grit scratch tests is the scratching force. It should be measurable in two components. The very short time during which the grain, or grit, makes contact with the specimen calls for a high-frequency force-measuring system.

Experience has shown that such tests are economically justifiable only when the specimens are of adequate size and scratches of sufficient length can be made. Force measurement below the workpiece must therefore be ruled out since the requirement that the force-measuring system have a high natural frequency allows only very small additional masses. Based on that requirement, one object of the invention is to provide an apparatus in which the force-measuring system is located below the abrasive grain on the rotating scratching disk.

Of special importance in the performance of single-grit scratch tests is the preparation of the specimen. Such tests can yield useful results only if the infeed is maintained perfectly constant during the scratching process. The amount of infeed in scratching usually is not more than a few microns ($\mu$). What accounts for the magnitude of the scratching force is the maximum depth of cut, which generally is from one to two powers of ten lower than the amount of the infeed. Since the depth of cut necessarily varies with the infeed, the scratching force also reacts very definitely to any change in the infeed.

In the scratching of a specimen, an increase in the force is observed at the end of the specimen even with a cross-feed error of $5\mu$. This shows that the decrease in the force in the center of the specimen is due, not to a wearing down of the grain but clearly to the cross-feed error. Thus it is apparent that a satisfactory cross feed of the specimen is essential if the single-grit scratch test is to yield reliable results. In contrast to the force pattern in the scratching of specimens with cross-feed errors, the force pattern generated in the scratching of specimens with good cross feed is substantially constant.

Prior-art single-grit scratching devices generally are devices resembling grinding wheels to whose periphery the grain to be tested is suitably secured. The tests are usually carried out on surface grinding machines.

Apparatuses are known in which the scratching force is measured in addition to the shape of the scratch made and in which the force-measuring means are disposed beneath the workpiece. The very short rise time of the force signals (about 50 $\mu$sec) usually makes it necessary to use piezoelectric quartz crystals. However, for the reasons stated a sufficiently high natural frequency can be obtained even with such basically very high-frequency dynamometers only when the additional mass of workpiece and holding fixture resting on the quartz crystal is very small. This is why apparatuses where the force-measuring system is disposed beneath the workpiece can only be used to scratch very small workpieces. These tests are time-consuming since the workpieces must be replaced frequently.

When a force-measuring system is used, scratch tests run with workpieces of any size will yield sufficiently meaningful results only if the force-measuring element is located on the periphery of the rotating scratching disk along with the very light-weight abrasive grain. An apparatus which in this respect is the most advanced has been described by C. H. Shen in an unpublished report of General Motors Manufacturing Development entitled "Single-grit grinding tests". The scratching device described by Shen consists of an aluminum disk and is provided with a piezoelectric force-measuring system. The grains undergoing testing are held in a clamp or are bonded to the disk with a synthetic-resin adhesive.

In the prior art which served as the point of departure for the invention, the specimen is surface-ground with a grinding wheel or belt grinder by rough-grinding, finish-grinding and polishing. The grinding wheel or support wheel must then be replaced with the scratching device, which has the drawback that running the test is time-consuming and uneconomical. On the other hand, if specimen preparation and scratching are done on separate machines, difficulties may be encountered due to the cross-feed error of the machine and in clamping the specimen.

In WEAR 19 (1972), pp. 303–304, D. Graham and R. M. Baul point out that the surface treatment may be carried out on the workpieces held on the machine table in situ before the start of the tests. With this in situ method the workpiece has to be clamped but once for both its preparation and scratching, although frequent changes of scratching disk and grinding wheel are necessary. Thus the specimen could first be rough-ground with a grinding wheel and then scratched without being remounted. In that case, however, the grinding wheel would have to be removed from the spindle and the scratching disk would then have to be mounted on the spindle, which entails considerable expenditure of time. In fact, it might be necessary to replace the grinding wheel repeatedly before the scratch test is run since the extremely high surface quality which the specimen to be scratched must possess cannot be achieved with a single grinding wheel.

Thus it is a further object of the invention to make it possible to carry out specimen preparation and scratching on just one machine without changeover.

Figure 2:
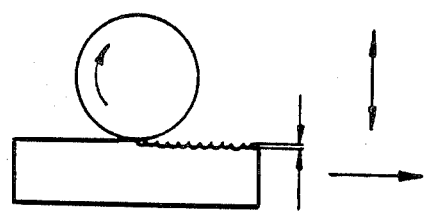

FIGS. 1 and 2 diagramatically depict a scratching process and the grain undergoing testing.

FIG. 3 depects the detailed construction of a preferred embodiment of the apparatus of the invention.

FIG. 4 is a diagramatic representation of the scratching device of the invention.

In accordance with the invention, this object is accomplished through a combination of a belt grinder and a scratching device comprising a support disk 3, mounted by means of a main flange 1 and a counter-flange 2, and a scratching disk (5) mounted on said main flange and carrying a single grain secured to its periphery along with a force-measuring system disposed thereunder, the whole forming a structural unit to be mounted on the spindle of the surface grinder, with a belt tensioning arm mounted on the headstock.

In a further embodiment of the invention, the force-measuring system is a combination of grain holder, piezoelectric quartz crystal 18, necked-down titanium bolt 8 with quick-acting tightening means, and transmission unit 6 and 7 disposed on the scratching device.

The chief advantages offered by the invention are time savings, minimization of the machine cross-feed error, extreme infeed constancy, and rapid and economical specimen preparation. As a result, it becomes possible to keep the depth of cut in scratching both very shallow and extremely constant. The construction of the apparatus of the invention will now be described in greater detail with reference to FIG. 3 of the drawing.

The main flange, whose dimensions correspond to those of a grinding-wheel flange and which permits the apparatus to be mounted on the spindle of a surface grinder and fixed by fitting key groove 13, is designated 1. The counterflange 2 permits the support disk 3 to be held in place. Said support disk is fitted with a rubber covering 21 having a Shore hardness of 95. Thus it can be adapted through a belt change for any finishing operation from roughing to polishing. Main flange 1, support disk 3, counterflange 2, rubber covering 21 and fillister-head screw 17 with a hexagonal recess form an independently rotatable unit. A dovetail groove in the counterflange 2 permits the apparatus to be balanced. The overall apparatus is provided with two balancing grooves. Dynamic unbalance can thus be avoided, which is important in a set of disks.

The main flange 1 is provided on its front face with a cone having a fitting key groove 12. Onto said cone the inner flange 4 of the scratching disk is set and secured by means of screws 16 to the counterflange. Like the other flanges, the inner flange 4 is made of steel and provided with a dovetail groove for balancing. The scratching disk 5 itself is fabricated from aluminum and mounted on the inner flange. A mount 6 for a force-signal transmitter is also bolted to the inner flange. The scratching disk comprises two segments which can be unscrewed from the main flange. This permits different force-measuring systems and grain holders to be mounted without the usually calibrated and prestressed force-measuring system having to be disassembled.

The scratching force is measured in up to three components by means of the piezoelectric quartz crystal. The latter is prestressed to the requisite initial stress by means of a necked-down bolt 8 made of titanium together with nut 20. The head of the necked-down bolt is provided with a conical recess and with an internal thread into which a clamping plate can be screwed. The grain holder is made of a special nickel-based alloy to which abrasive grains can be bonded by means of a solder glass. The conical foot of the grain holder is seated in the conical recess in the necked-down bolt and secured thereto by means of the clamping plate. The grain can thus be positioned as desired and is adequately secured to the necked-down bolt. The requisite natural frequency of the force-measuring system is obtained by the use of titanium and the careful design of the necked-down bolt and of the tightening means. The apparatus of the invention further comprises a belt tensioning arm with an idler pulley (not shown in FIG. 3.) Suitable force-signal transmitters are, for example, rotary mercury transmitters or telemetric measuring systems. Shown in FIG. 3 is a rotary transmitter 7.

In actual tests with the apparatus of the invention, the grain being tested is secured to and positioned on the periphery of the scratching disk. The charge signals of the normal and tangential forces are transmitted from the piezoelectric force-measuring system through the rotary transmitter to charge amplifiers and recorded with a storage oscillograph, one of the force signals indicating the normal force pattern and the other the tangential force pattern. The infeed is set at $40\mu$ by "aiming at" the grain in the center of the workpiece without moving the machine table. This will indicate to the eye of the observer the first contact of the grain with the workpiece and can also be recorded through the low force indicated at the storage oscillograph. Then the position of the machine table on which the surface-ground workpiece is located is changed so that the scratching process sets in at the forward end of the workpiece. While the scratching disk is rotating in a clockwise direction during the scratching operation, the table executes a working stroke in the same or in the opposite direction. The infeed remains constant. In this way, a scratch is made in the workpiece surface.

As many as four evenly spaced scratches are made unless the grain wears down before thay can be completed. Then the grain is replaced and set aside for evaluation. FIG. 4 is a diagrammatic representation of the scratching device of the invention. In this representation, the following parts of the apparatus of the invention are shown: Headstock 30, grinder spindle 31, abrasive grain 32, force transducer 18, rotary transmitter 7, mount 6, scratching disk 5, support disk 3, grinding or polishing belt 38, belt tensioning arm 39, idler pulley 40, and compression spring 43.

It will be understood that the specification and examples are illustrative but not limitative of the present invention and that other embodiments within the spirit and scope of the invention will suggest themselves to those skilled in the art.

What is claimed is:

1. An apparatus for testing abrasive grains in single-grit scratch tests, suitable for mounting on a surface grinding machine, which comprises in combination a main flange and a counter flange, a belt grinder and a scratching device comprising a support disk mounted by means of said main flange and counter flange, a scratching disk mounted on said main flange and carrying a single grain secured to the scratching disk periphery and a force-measuring system disposed thereunder, the force measuring system comprising a necked-down bolt having a head and rapid action tightening means; a grain holder supported at the head of the bolt, and a piezo-electric quartz crystal prestressed by said bolt to measure the force, the entire apparatus forming a structural unit adapted to be mounted on the spindle of a surface-grinding machine, a headstock, said spindle extending from the headstock, and a belt tensioning arm mounted on the headstock.

2. The apparatus of claim 1, wherein the bolt is titanium.

* * * * *